US006616615B2

(12) United States Patent
Mault

(10) Patent No.: US 6,616,615 B2
(45) Date of Patent: Sep. 9, 2003

(54) RESPIRATORY CALORIMETER

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 0 days.

(21) Appl. No.: 10/057,651

(22) Filed: Oct. 29, 2001

(65) Prior Publication Data

US 2002/0095096 A1 Jul. 18, 2002

Related U.S. Application Data

(63) Continuation of application No. 09/008,435, filed on Jan. 16, 1998, now Pat. No. 6,309,360.
(60) Provisional application No. 60/042,079, filed on Mar. 28, 1997, and provisional application No. 60/041,594, filed on Mar. 17, 1997.

(51) Int. Cl.[7] ................................................ A61B 5/08

(52) U.S. Cl. ..................... 600/531; 600/532; 600/538

(58) Field of Search ............................ 600/529, 531, 600/532, 538, 533; 128/200.24

(56) References Cited

U.S. PATENT DOCUMENTS

| | | | | |
|---|---|---|---|---|
| 2,826,912 A | 3/1958 | Kritz | ............................ | 73/194 |
| 2,831,348 A | 4/1958 | Kritz | ........................ | 73/861.28 |
| 2,869,357 A | 11/1959 | Kritz | ............................. | 73/32 |
| 2,911,825 A | 11/1959 | Kritz | ............................ | 73/194 |
| 3,220,255 A | 11/1965 | Scranton et al. | ............... | 73/204 |
| 3,962,917 A | 6/1976 | Terada | ........................ | 73/204 |
| 4,078,554 A | 3/1978 | Lemaitre et al. | ............ | 128/2.08 |
| 4,197,857 A | 4/1980 | Osborn | ........................ | 600/531 |
| 4,425,805 A | 1/1984 | Ogura et al. | .............. | 73/861.29 |
| 4,440,177 A | 4/1984 | Anderson et al. | ............ | 600/532 |
| 4,463,764 A | 8/1984 | Anderson et al. | ............ | 600/532 |
| 4,648,396 A | 3/1987 | Raemer | ........................ | 600/534 |
| 4,658,832 A | 4/1987 | Brugnoli | ....................... | 600/532 |
| 4,796,639 A | 1/1989 | Snow et al. | ................. | 600/532 |
| 4,850,371 A | 7/1989 | Broadhurst et al. | .......... | 600/532 |
| 4,856,531 A | 8/1989 | Merilainen | ................... | 600/532 |
| 4,859,858 A | 8/1989 | Knodle et al. | ............... | 250/504 |
| 4,859,859 A | 8/1989 | Knodle et al. | ............... | 250/504 |
| 4,909,259 A | 3/1990 | Tehrani | ........................ | 600/531 |
| 4,914,720 A | 4/1990 | Knodle et al. | ............... | 250/343 |
| 4,914,959 A | 4/1990 | Mylvaganam et al. | ... | 73/861.28 |
| 4,917,108 A | 4/1990 | Mault | ............................ | 65/273 |
| 4,955,946 A | 9/1990 | Mount et al. | ................ | 600/532 |
| 4,958,075 A | 9/1990 | Mace et al. | .................. | 250/343 |
| 4,986,268 A | 1/1991 | Tehrani | ........................ | 128/204 |
| 4,998,018 A | 3/1991 | Kurahashi et al. | ........... | 250/343 |
| 5,038,773 A | 8/1991 | Norlien et al. | .......... | 128/205.23 |
| 5,038,792 A | 8/1991 | Mault | .......................... | 128/718 |
| 5,042,500 A | 8/1991 | Norlien et al. | ............... | 600/532 |
| 5,042,501 A | 8/1991 | Kenny et al. | ................ | 600/532 |
| 5,060,506 A | 10/1991 | Douglas | ......................... | 73/24.1 |
| 5,060,655 A | 10/1991 | Rudolph | ....................... | 128/716 |
| 5,081,871 A | 1/1992 | Glaser | ....................... | 73/863.23 |
| 5,095,900 A | 3/1992 | Fertig et al. | ............ | 128/704.14 |
| 5,117,674 A | 6/1992 | Howard | ....................... | 73/31.07 |

(List continued on next page.)

Primary Examiner—Max F. Hindenburg
Assistant Examiner—Navin Natnithithadha
(74) Attorney, Agent, or Firm—Gifford, Krass, Groh, Sprinkle, Anderson & Citkowski, P.C.

(57) ABSTRACT

An indirect calorimeter for measuring the subject's oxygen consumption per unit time employs a mouthpiece through which the subject breathes for a period of time. Conduits connect the mouthpiece to a flow meter and a capnometer so that the subject's inhalations and exhalations pass through the flow meter and the exhalations also pass through the capnometer. Electrical signals from the flow meter and capnometer are provided to a computer which calculates the $CO_2$ exhaled by the subject during the test by integrating the instantaneous $CO_2$ content of an exhalation as measured by the capnometer over the volume as measured by the flow meter and subtracts that quantity from the exhaled volume and subtracts their difference from the inhaled volume. In alternative embodiments the system can also measure the subject's Cardiac Output and Delivered Oxygen.

17 Claims, 2 Drawing Sheets

U.S. PATENT DOCUMENTS

| | | | |
|---|---|---|---|
| 5,119,825 A | 6/1992 | Huhn | 600/529 |
| 5,178,155 A | 1/1993 | Mault | 128/718 |
| 5,179,958 A | 1/1993 | Mault | 128/718 |
| 5,214,966 A | 6/1993 | Delsing | 73/861.28 |
| 5,233,996 A | 8/1993 | Coleman et al. | 600/529 |
| 5,282,473 A | 2/1994 | Braig et al. | 600/532 |
| 5,299,579 A | 4/1994 | Gedeon et al. | 600/532 |
| 5,303,712 A | 4/1994 | Van Duren | 600/529 |
| 5,309,921 A | 5/1994 | Kisner et al. | 600/532 |
| 5,326,973 A | 7/1994 | Eckerbom et al. | 250/343 |
| 5,357,972 A | 10/1994 | Norlien | 128/725 |
| 5,363,857 A | 11/1994 | Howard | 600/531 |
| 5,398,695 A | 3/1995 | Anderson et al. | 600/532 |
| 5,419,326 A | 5/1995 | Harnoncourt | 128/660.02 |
| 5,425,374 A | 6/1995 | Ueda et al. | 600/532 |
| 5,450,193 A | 9/1995 | Carlsen et al. | 356/301 |
| 5,503,151 A | 4/1996 | Harnoncourt et al. | 128/660.02 |
| 5,647,370 A | 7/1997 | Harnoncourt | 128/725 |
| 5,676,132 A | 10/1997 | Tillotson et al. | 128/204.23 |
| 5,705,735 A | 1/1998 | Acorn | 73/23.3 |
| 5,743,253 A | 4/1998 | Castor et al. | 128/200 |
| 5,754,288 A | 5/1998 | Yamamoto et al. | 356/301 |
| 5,789,660 A | 8/1998 | Kofoed et al. | 73/232 |
| 5,796,009 A | 8/1998 | Delsing | 73/861.28 |
| 5,800,360 A | 9/1998 | Kisner et al. | 600/532 |
| 5,816,246 A | 10/1998 | Mirza | 128/726 |
| 5,831,175 A | 11/1998 | Fletcher-Haynes | 73/861.28 |
| 5,834,626 A | 11/1998 | De Castro et al. | 73/23.3 |
| 5,836,300 A | 11/1998 | Mault | 128/204.23 |
| 5,922,610 A | 7/1999 | Alving et al. | 436/116 |
| 5,932,812 A | 8/1999 | Delsing | 73/861.02 |
| 5,957,858 A | 9/1999 | Micheels et al. | 600/532 |
| 6,010,459 A | 1/2000 | Silkoff et al. | 600/532 |
| 6,044,843 A | 4/2000 | O'Neil et al. | 128/204.23 |
| 6,135,107 A * | 10/2000 | Mault | 128/204.23 |
| 6,309,360 B1 * | 10/2001 | Mault | 600/531 |

* cited by examiner

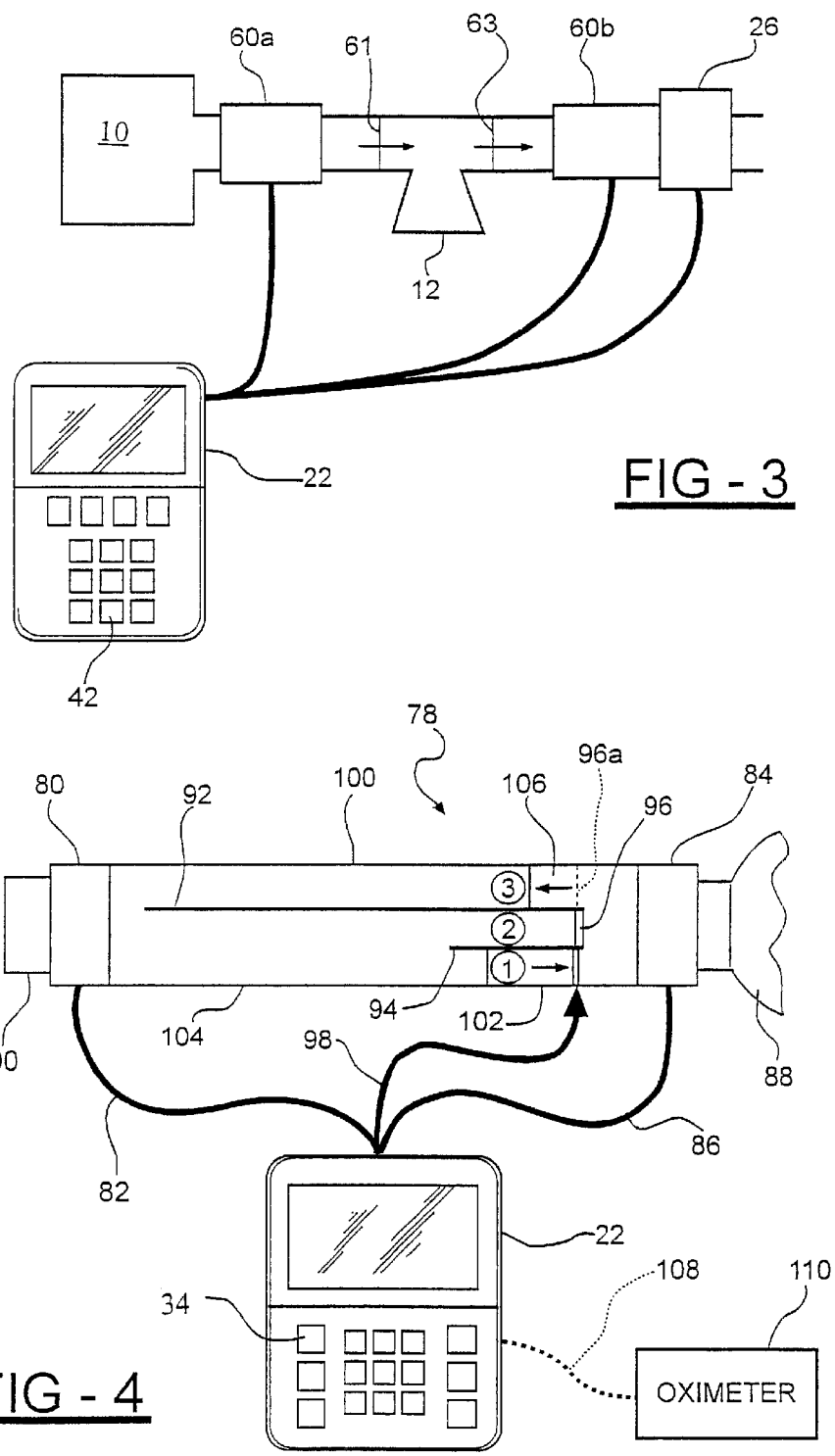

RESPIRATORY CALORIMETER

RELATED APPLICATIONS

This application is a continuation of U.S. patent application Ser. No. 09/008,435, filed Jan. 16, 1998, now U.S. Pat. No. 6,309,360, which claims the benefit of Provisional Patent Application Ser. Nos. 60/041,594 and 60/042,079, filed Mar. 17, 1997 and Mar. 28, 1997, respectively.

FIELD OF THE INVENTION

This invention relates to indirect calorimeters for determining the metabolic rates of subjects by measuring their oxygen consumption during respiration over a period of time, and more particularly to such a calorimeter employing a flow meter and a capnometer to compute the difference between the inhaled gas volume and the volume of the exhaled gas less the exhaled $CO_2$ volume.

BACKGROUND OF THE INVENTION

Measurement of the energy expenditure of humans is important for a number of reasons, including the determination of the proper caloric content for feedings of hospitalized patients whose metabolisms may deviate from normal values, the monitoring of progress of weight loss diets to allow the adjustment of caloric inputs to achieve a target loss and the determination of energy expenditure during exercise.

A variety of indirect calorimeters for measuring oxygen consumption during respiration have been devised. One form of respiratory calorimeter, disclosed in my U.S. Pat. Nos. 4,917,108; 5,038,792; 5,179,985 and 5,178,155, measures the volume of a subject's inhalations over a period of time, and the volume of the subject's exhalations after carbon dioxide in the exhalations has been removed by an absorbent scrubber. These measurements are integrated over the time of measurement and the difference between the two summed volumes is a measure of the subject's oxygen consumption. This follows from the fact that inhaled oxygen is either absorbed into the blood in the subject's lungs or expelled during exhalation. Some portion of the blood absorbed oxygen is replaced with $CO_2$. When the $CO_2$ is removed from the exhaled volume, the summed difference between inhalation and exhalation volume over a period of time is equal to the absorbed oxygen.

In some versions of these prior calorimeters a capnometer was also used to measure the instantaneous value of the exhaled $CO_2$ in a breath allowing the calculation of $CO_2$ production, Resting Energy Expenditure (REE) and Respiratory Quotient (RQ).

The absorbent scrubber used with these previous systems, such as sodium hydroxide or calcium hydroxide, which reacts with the $CO_2$ to form water plus a salt, has a limited ability to absorb $CO_2$ and must be replenished after a period of use. The scrubber is also large and heavy relative to the other components of the calorimeter.

SUMMARY OF THE PRESENT INVENTION

The present invention eliminates the need for the carbon dioxide scrubber used in my previous devices by measuring the volume of exhaled carbon dioxide and subtracting that volume from the total exhaled volume over the measurement period to calculate a sum which is then subtracted from the inhaled volume to arrive at $VO_2$. The volume of exhaled carbon dioxide is preferably measured by integrating the instantaneous carbon dioxide percentage of the exhalation, as measured by a capnometer, over the exhaled volume as measured by a flow meter: $VCO_2 = V_e(\%CO_2)$.

The flow meter generates an electrical signal as a function of the instantaneous flow volume and this signal is preferably sent to microprocessor-based computer along with the electrical output of a capnometer sensor. A preferred embodiment of the invention uses a bidirectional flow meter to measure both the inhaled and exhaled flow volume. A temperature and/or humidity conditioner may be utilized to equalize the temperature and/or humidity of the incoming air to that of the exhaled air so that uniform flow measurements may be made. Alternatively, the system could receive signals representing temperature, humidity and/or barometric pressure from sensors disposed in the calorimeter or externally, or keyboard entries and calculate correction factors for the flow measurement based on the signals. In this configuration the distinction between inhalations and exhalations is determined by the presence or absence of $CO_2$ in the flowing gas is measured by the capnometer or by a zero crossing algorithm applied to the output of the flow meter.

Alternatively, the invention might employ a unidirectional flow sensor and conduits and one-way valves arranged so that both the inhaled flow volume and the exhaled flow volume pass through the flow meter in the same direction possibly providing a more precise flow measurement than the bidirectional flow sensor of the preferred embodiment.

The microprocessor, in addition to calculating and displaying the $VO_2$, may calculate and display REE, RQ and the rate of carbon dioxide production.

Another alternative embodiment of my invention may be used to calculate the subject's Cardiac Output implementing the noninvasive method of cardiac output measurement using partial $CO_2$ rebreathing described in an article by Capek and Roy in *IEEE Transactions and Biomedical Engineering*, Vol. 35, pages 653–61, 1988. This embodiment of the invention employs a two stage measurement. In the first stage, the device is configured in essentially the same manner as the other embodiments of the invention to measure oxygen consumption. Over a period of use, such as three minutes, the microprocessor measures $VO_2$, $VCO_2$, and the end-tidal $CO_2$ ($etCO_2$) which is the carbon dioxide content of a breath at the end of an exhalation. These values are stored and the device is then switched to a configuration in which the end portion of each exhalation is not expelled from the device but is rather captured so that it forms the initial portion of the gas provided to the subject during the next inhalation. This is achieved by creating a dead space chamber in the exhalation passage. The subject breathes in this manner for a short period such as 30 seconds. During this period the breath-to-breath $etCO_2$ and the total $VCO_2$ are recorded. The computer then implements the calculation:

$$C.O. = \frac{\Delta_{VCO_2}}{\Delta_{etCO_2}}$$

where $\Delta VCO_2$ equals the difference in the total volume of exhaled $CO_2$, per breath, during the two recordings and $\Delta etCO_2$ is the difference in the end-tidal $CO_2$ between the two recordings.

BRIEF DESCRIPTION OF THE DRAWINGS

Other advantages and applications of the present invention will be made apparent by the following detailed description of several embodiments of the invention. The description makes reference to the accompanying drawings in which:

FIG. 3 is an embodiment of the indirect calorimeter employing two unidirectional flow meters; and FIG. 4 is a schematic diagram of another embodiment of the invention constituting an oxygen consumption system and cardiac output measurement system.

DETAILED DESCRIPTION OF THE INVENTION

Figure 1:
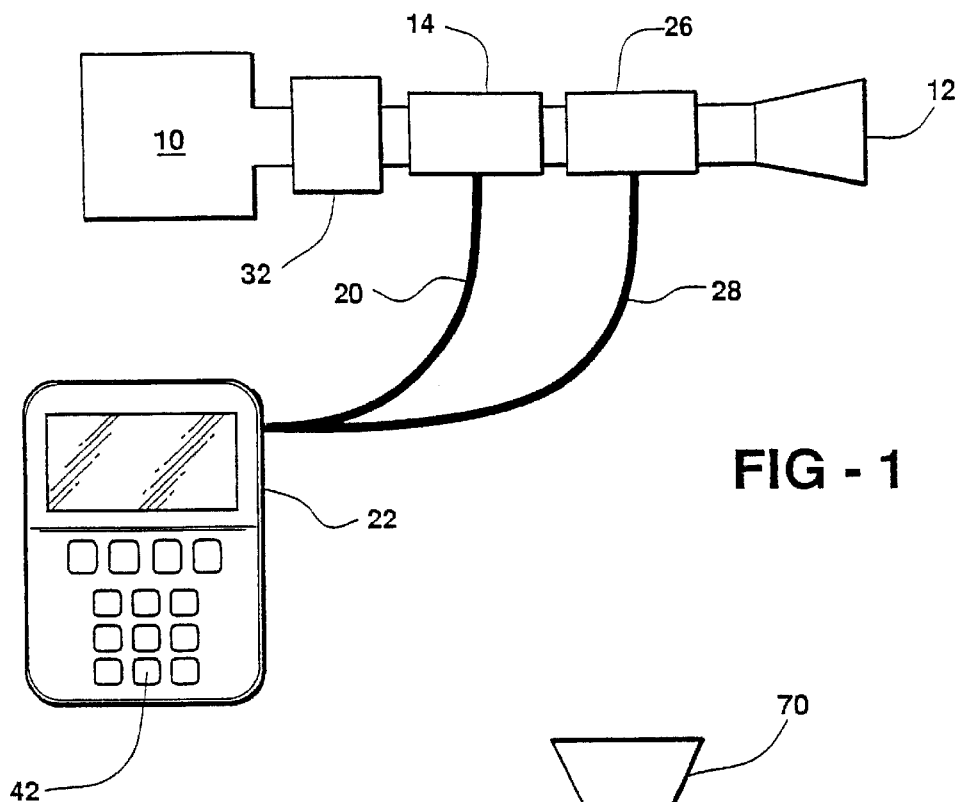
FIG. 1 is a schematic diagram of a preferred embodiment of my invention constituting a respiratory calorimeter employing a bidirectional flow meter and a capnometer providing electrical outputs to a microprocessor-based computer.

Referring to FIG. 1, which schematically illustrates a preferred embodiment of the present oxygen consumption meter, a source of respiratory gases, which may be ambient air or some form of positive-pressure ventilator is schematically illustrated at 10. A subject or patient whose respiratory finction is being measured breathes through a respiratory connector taking the form of a mouthpiece 12 adapted to engage the inner surfaces of the user's mouth so as to form the sole passage for inhaled and exhaled air passing through the mouth. A nose clamp (not shown) of conventional construction may be employed to assure that all the respiratory air passes through the mouthpiece 12. In alternative configurations a mask that engages the nose as well as the mouth might be employed.

The system employs a bidirectional flow meter 14, preferably of the pressure differential type such as manufactured by Medical Graphics Corporation of St. Paul, Minn. under the trademark "MEDGRAPHICS". Alternatively, other forms of flow transducers might be used such as a differential temperature type. The flow meter 14 is designed to accurately measure gases flowing from the device in either direction. The flow meter provides two separate tubular lines 20 to a pair of pressure transducers disposed within a microprocessor-based computation and display unit 22.

One end of the flow meter 14 is connected to a capnometer 26. The capnometer is operative to generate an electrical signal which is a function of the percentage of $CO_2$ concentration in the gas volume which it passes. The capnometer may be of a conventional type such as those described in U.S. Pat. Nos. 4,859,858; 4,859,859; 4,914,720; or 4,958,075. The electrical signal from the capnometer is provided to the microprocessor-based computer 22 over line 28.

Novametrix Medical Systems Inc. of Wallingford, Conn. manufactures a respiratory profile monitor employing a combined capnometer and flow sensor which could be used with the present invention. The other end of flow meter 14 is connected to a temperature and/or humidity conditioner unit 32. This unit acts to operate upon inhaled respiratory gases to bring either or both their moisture content or temperature into close alignment with the exhaled gases to improve the accuracy of the flow measurement made by the meter 14. The humidity conditioning function may be provided by a moisture absorbing filter such as a filter formed of fiber cellular material or a sponge, of the type termed a "artificial nose". This unit acts to absorb water vapor from gases passing through it if the water vapor content of the gases is higher than the level of moisture contained in the filter or to add water vapor to the gases if the filter vapor level is higher than that of the gases. Since the unit 32 passes both the inhaled gases and the exhaled gases, it tends to equalize them. The unit might also incorporate an active heating element to bring cooler gases from the respiratory source up to the body temperature of the exhalations.

Alternatively, the system could receive signals representing barometric pressure, room temperature, and humidity from sensors or keyboard entries and calculate correction factors for the flow measurement based on these signals. The distinction between inhalations and exhalations may be determined by the presence or absence of $CO_2$ in the flowing gas is measured by the capnometer alone or in combination with analysis of the flow meter signal by a zero crossing algorithm.

The other end of the conditioner unit 32 is connected to the respiratory gas source 10. Accordingly, upon the subject inhaling, gas is drawn through the chain of the temperature/humidity compensator 32, the capnometer 26 and the flow meter 14 from the source of respiratory gases 10. Exhalations pass through the chain of elements 32, 26 and 14 in the reverse direction.

The microprocessor-based computation and display unit 22 receives the two pressure signals from the flow meter via line 20 and from the capnometer via line 28. During a test, typically lasting 3–5 minutes, the microprocessor-based computer 22 integrates the signals from the flow meter 14 during inhalations and similarly integrates the flow meter readings during exhalations. The unit 22 may also generate a signal representative of the total volume of $CO_2$ exhaled during the test period by multiplying the percentage $CO_2$ signal on line 28 with the volume signal on line 20 and integrating the value over the test. The computer 22 can then calculate and display the oxygen consumption per unit time $VO_2$ by subtracting the exhaled $CO_2$ volume from the total exhaled volume and subtracting their difference from the inhaled volume. It can also display the exhaled $CO_2$ volume. The computer 22 preferably operates on a digital basis and if the signals on lines 20 and 28 are analog signals, as they are in the preferred embodiment of the invention, it digitizes those signals. A keyboard 42 associated with the computer 22 allows the storage and display of various factors in the same manner as the systems of my previous patents.

In addition to calculating the oxygen consumption of the subject, $VO_2$, and the resting energy expenditure in kilocalories per unit time, the computer 22 preferably generates a display of the exhaled $CO_2$ volume per unit time, RQ, which equals $VCO_2/VO_2$ and REE preferably calculated from the Weir equation: REE(KC/24 hours)=$1440(VO_2 \times 3.341) + (VCO_2 \times 1.11)$ where $VO_2$ and $VCO_2$ are both measured in milliliters per minute.

Figure 2:
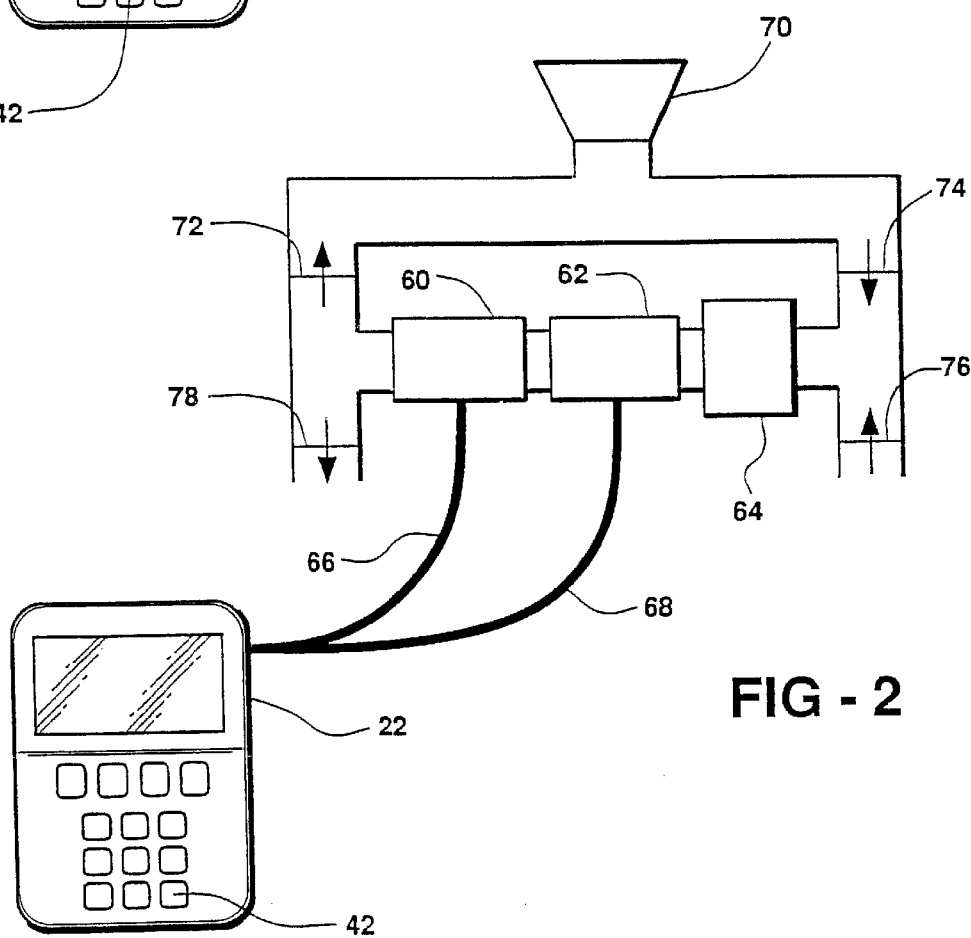
FIG. 2 is a schematic diagram of a respiratory calorimeter representing an alternative embodiment of the invention utilizing a unidirectional flow meter and conduits and valvings which direct the subject's inhalations and exhalations through the flow meter in the same direction.

An alternative embodiment of the calorimeter, illustrated in FIG. 2, employs a unidirectional flow meter 60 connected by conduits between a capnometer sensor 62 and a temperature and/or humidity conditioner 64. The flow meter 60 provides a pair of pressure signals on line 66 to appropriate transducers disposed within a microprocessor-based computer 22 having a keyboard 42 and a display. The capnometer 62 provides an electrical output signal on line 68 to the computer 22. A patient connection such as a mouthpiece 70 receives inhaled gas from the output of the flow meter 60 via a one-way valve 72. Exhalations through the mouthpiece 70 are passed by a one-way valve 74 to the inlet of the conditioner 64. The respiratory gas inlet to the device, from the ambient air or a ventilator, is through a one-way valve 76, and the outlet of the device back to that source is through a fourth one-way valve 78.

Upon the subject inhaling through the connector 70, respiratory gases are drawn in through the valve 76, pass through the series chain of the conditioner 64, capnometer 62 and flow meter 60, and are directed by the valve 72 to the mouthpiece 70. Upon exhalation the valve 72 blocks flow so that gases pass through the valve 74, through the chain 64, 62, and 60 in the same direction as the inhalation, and through the valve 78 to the source of respiratory gases since the exhalation pressure on the outlet side of valve 72 prevents flow in that direction.

In both of these embodiments it should be understood that the use of temperature and/or humidity conditioning is optional and if used is intended to improve the precision of the measurements.

Another embodiment of the invention, illustrated in FIG. 3, employs two unidirectional flow meters 60a and 60b, both connected to a computer 22. The outlet of flow meter 60a is connected to the mouthpiece 12 through a one-way valve 61 and the output of the mouthpiece 12 is connected to the inlet of the second flow meter 60b via a second one-way valve 63. The output of flow meter 60b passes through a capnometer 26 to the source 10. The capnometer is also connected to the computer.

This embodiment is simple and provides the accuracy of unidirectional flow meters.

An alternative embodiment of the invention illustrated in FIG. 4 allows the measurement of the subject's Cardiac Output (CO) as well as oxygen consumption and the other parameters measured by the previous embodiments of the invention. Like the embodiment of FIG. 1, the system of FIG. 4 employs a bidirectional volume flow meter 80 operative to provide pressure signals as a function of the instantaneous gas flow volume through it on line 82 to transducers forming part of a microprocessor-based computer and display unit 22 having an input keyboard 34. It also employs a capnometer sensor 84 which provides an electrical output representative of the instantaneous percentage of $CO_2$ in the gas passing through the capnometer, on line 86 to the microprocessor-based computer 22.

One side of the capnometer is connected to a respiratory connector mouthpiece 88. One side of the bidirectional volume flow meter 80 is connected to a source of respiratory gases 90 which is preferably ambient air. The unit could incorporate humidity and/or temperature sensors like the other embodiments or the microprocessor could make calculations based on ambient temperature, barometric pressure and humidity to compensate the flow sensor readings.

The passageways interconnecting the flow meter 80 and the capnometer 84 include a partition wall 92 extending from near one end of the flow meter 80 to near one end of capnometer sensor 84. A shorter partition 94 extends parallel to the partition 92 adjacent the capnometer sensor. A switchable partition 96 may be controlled by a signal on line 98 from the microprocessor 22 to move between the illustrated position in which it extends between the two ends of the partitions 92 and 94 and blocks flow between them, and an alternative position, illustrated in phantom lines as 96 a where it unblocks the space between the partitions 92 and 94 and instead blocks the space between one end of the partition 92 and wall 100 of the conduit interconnecting the flow meter 80 and the capnometer 84.

To make a measurement of oxygen consumption, the partition 96 is switched to the position illustrated in FIG. 4 in which it extends between the ends of the partitions 92 and 94 and blocks the passage of gases between them. When the subject inhales through the mouthpiece 88, respiratory gases are drawn from the source 90 through the bidirectional flow meter 80 and through a one-way valve 102 which extends between the partition 94 and the conduit wall 104. Exhalations through the mouthpiece 88 pass through the capnometer 84 and then through a one-way valve 106 which extends between the end of the partition 92 near the capnometer and the wall 100 of the conduit. Then the exhalations pass out the bidirectional flow meter 80 to the source of respiratory gases 90.

Like the embodiments of FIGS. 1 and 2, the computer 22, receiving signals from the flow sensor and the capnometer, generates the signal $VO_2$ by subtracting the exhalation flow volume, less the volume of $CO_2$ in the exhalation, as calculated by integrating the instantaneous $CO_2$ signal from the capnometer 84 over the exhalation flow signal from the flow sensor 80, from the inhalation volume as measured by the flow meter 80. REE and RQ may be calculated in the same manner as in the previous embodiments.

The unit may be used to calculate Cardiac Output in the same manner as the combined oxygen and cardiac output analyzer disclosed in my pending U.S. patent application filed on Mar. 11, 1997. This implements the nonevasive method of cardiac output measurement using $CO_2$ rebreathing described in an article by Capek and Roy in the *IEEE Transactions in Biomedical Engineering*, Volume 35, pages 653–61, 1988. Essentially, with the partition 96 in the position illustrated in FIG. 4, $VO_2$, $VCO_2$, and end-tidal $CO_2$ ($etCO_2$) are recorded over 3 minutes. The occurrence of the end-tidal time is detected by examining the output of either the flow sensor or the capnometer. The partition 96 is then switched so that the input to valve 106 is blocked. During exhalation, a portion of the exhaled breath is stored in the volume between the partition 92 and the wall 104. When the user inhales, the initial portion of the inhalation constitutes this previously breathed gas and the balance is drawn from the respiratory gas source 90 through the bidirectional volume flow meter 80. During this period, the breath-to-breath $etCO_2$ and total $VCO_2$ are recorded. The computer 22 then implements the calculation:

$$C.O. = \frac{\Delta_{VCO_2}}{\Delta_{etCO_2}}$$

where $\Delta VCO_2$ equals the difference in the total volume of exhaled $CO_2$, per breath, during the two recordings and $\Delta etCO_2$ is the change in the end-tidal $CO_2$ content of an exhalation between the first recording and the second recording, with the end-tidal point detected by a zero crossing algorithm in the microprocessor.

FIG. 4 illustrates an alternative embodiment in which line 108 provides the output signal from a continuous pulse oximeter 110, preferably of the type attached to a subject's finger, to allow the measurement of Delivered Oxygen ($DO_2$). The measured or estimated hemoglobin value of the subject is entered via keyboard 24 by the operator. The computer then implements the equation:

$$DO_2 = (C.O.)(SpO_2)(Hgb)(1.36)[<]qa$$

where $SpO_2$ equals the blood oxygenation as measured by the oximeter 110.

Having thus disclosed my invention, I claim:

1. A respiratory analyzer, operative to determine a metabolic rate of a subject, comprising:
   a flow path, through which respiratory gases pass as the subject breathes through the respiratory analyzer;
   a flow meter operative to generate a flow signal as a function of a flow rate of gases passing through the flow path;

a capnometer operative to generate a capnometer signal as a function of an instantaneous carbon dioxide content of gases within the flow path; and an electronic computer operative to receive the flow signal from the flow meter and the capnometer signal from the capnometer, the electronic computer being operative to determine a carbon dioxide production, an oxygen consumption, and the metabolic rate of the subject, wherein the oxygen consumption is determined by subtracting a difference volume from an inhaled volume, wherein the difference volume is an exhaled volume minus an exhaled volume of carbon dioxide.

2. The respiratory analyzer of claim 1, wherein the inhaled volume is determined by a method comprising an integration over time of the flow signal as the subject inhales, and the exhaled volume is determined by a method comprising an integration over time of the flow signal as the subject exhales.

3. The respiratory analyzer of claim 1, wherein the exhaled volume of carbon dioxide is determined by a method comprising an integration over time of a product of the flow signal and the capnometer signal as the subject exhales.

4. The respiratory analyzer of claim 1, further comprising a pressure sensor, wherein the electronic computer receives a pressure signal from the pressure sensor.

5. The respiratory analyzer of claim 1, further comprising a humidity sensor, wherein the electronic computer receives a humidity signal from the humidity sensor.

6. The respiratory analyzer of claim 1, further comprising a temperature sensor, wherein the electronic computer receives a temperature signal from the temperature sensor.

7. The respiratory analyzer of claim 1, wherein the electronic computer is operative to determine the metabolic rate of the subject using the Weir equation.

8. The respiratory analyzer of claim 1, comprising a respiratory connector in fluid communication with the flow path, the respiratory connector operative to be supported in contact with the subject so as to pass respiratory gases as the subject breathes through the respiratory connector.

9. The respiratory analyzer of claim 8, wherein the flow path comprises conduits interconnecting the respiratory connector, the flow meter and the capnometer so that the subject's inhalations and exhalations pass through the flow meter and the subject's exhalations pass through the capnometer.

10. The respiratory analyzer of claim 8 further including a source of respiratory gases and a switch moveable between a first position wherein an inhalation draws through the respiratory connector gases which are substantially from the source of respiratory gases, and a second position wherein an inhalation provides to the respiratory connector an initial quantity of gases representing the gases expired during the previous exhalation and the balance of the gases during the inhalation constitute gases from the respiratory connector, and wherein the electronic computer is operative to determine the subject's Cardiac Output based upon signals generated while the switch was initially in the first position and then subsequently in the second position.

11. A respiratory analyzer, operative to determine a metabolic rate of a subject, comprising:

an inhalation path, through which inhaled gases pass as the subject breathes through the respiratory analyzer;

an exhalation path, through which exhaled gases pass as the subject breathes through the respiratory analyzer;

a flow meter operative to generate a flow signal as a function of a flow rate of inhaled gases and exhaled gases;

a capnometer operative to generate a capnometer signal as a function of an instantaneous carbon dioxide content of exhaled gases within the exhalation path; and an electronic computer operative to receive the flow signal from the flow meter and the capnometer signal from the capnometer, the electronic computer being operative to determine a carbon dioxide production, an oxygen consumption, and the metabolic rate of the subject as the subject breathes through the respiratory analyzer, wherein the oxygen consumption is determined by subtracting a difference between an exhaled volume and an exhaled carbon dioxide volume from an inhaled volume.

12. The respiratory analyzer of claim 11, wherein the inhalation path and exhalation path are the same.

13. The respiratory analyzer of claim 12, wherein the flow meter is a bi-directional flow meter.

14. A device for determining a cardiac output of a subject, the device comprising:

a flow path, through which respiratory gases pass as the subject breathes through the device;

a flow meter operative to generate a flow signal as a function of a flow rate of gases through the flow path;

a capnometer operative to generate a capnometer signal as a function of an instantaneous carbon dioxide content of gases within the flow path;

a switch, having a first position and a second position, the switch being operative in the first position to provide inhalation gases from a source of inhalation gases for inhalation by the subject, the switch being operative in the second position to pass exhaled gases from the flow path to a storage volume whereby the storage volume contains stored exhaled gases, and to provide-at least part of the stored exhaled gases for inhalation by the subject; and an electronic computer operative to receive the flow signal from the flow meter and the capnometer signal from the capnometer, to determine a carbon dioxide production and an end tidal carbon dioxide value of the subject, and to determine the cardiac output of the subject by comparing the subject's carbon dioxide production and end tidal carbon dioxide value before and after the switch is moved from the first position to the second position.

15. The device of claim 14, wherein the end-tidal carbon dioxide value is determined from the capnometer signal at points in time determined by a zero crossing algorithm applied to the flow signal.

16. The device of claim 14, wherein the source of inhaled gases is the atmosphere, and the switch is operative in the second position to provide a mixture of stored exhaled gases and atmospheric gases for inhalation by the subject.

17. The device of claim 14, wherein the electronic computer is further operative to receive a blood oxygenation value from a pulse oximeter in contact with the subject, and to determine a delivered oxygen value from the cardiac output value, the blood oxygenation value, and a measured or estimated hemoglobin value.

* * * * *